United States Patent [19]

Gregory, Jr. et al.

[11] Patent Number: 5,571,014

[45] Date of Patent: Nov. 5, 1996

[54] DISPOSABLE TORQUE LIMITING WRENCH

[75] Inventors: Franklin P. Gregory, Jr., Racine, Wis.; James W. Nelson, Morristown, N.J.

[73] Assignee: Snap-on Technologies, Inc., Crystal Lake, Ill.

[21] Appl. No.: 300,468

[22] Filed: Sep. 2, 1994

[51] Int. Cl.$^6$ ........................................... A61C 3/00
[52] U.S. Cl. ............................... 433/141; 433/126
[58] Field of Search ......................... 433/141, 126–129, 433/163, 174, 225, 155; 81/474, 475, 476, 473, 472, 477, 467

[56] References Cited

U.S. PATENT DOCUMENTS

| | | | |
|---|---|---|---|
| 2,378,956 | 6/1945 | Thorner | 81/475 |
| 2,600,327 | 6/1952 | Ridge | 81/474 |
| 2,797,564 | 7/1957 | Bonneau et al. | 464/58 |
| 2,893,278 | 7/1959 | Rice | 81/467 |
| 2,948,173 | 8/1960 | Herrmann | 81/477 |
| 3,425,314 | 2/1969 | Ohlson | 81/474 |
| 3,662,628 | 5/1972 | Schnepel | 81/474 |
| 3,960,039 | 6/1976 | Nash et al. | 81/475 |
| 4,015,335 | 4/1977 | Nash et al. | 32/27 |
| 4,090,421 | 5/1978 | Czeczerski | 81/52.4 |
| 4,131,039 | 12/1978 | Garconnet | 81/475 |
| 4,313,725 | 2/1982 | Lieb et al. | 433/126 |
| 5,158,458 | 10/1992 | Perry . | |
| 5,368,480 | 11/1994 | Balfour et al. | 433/141 |

OTHER PUBLICATIONS

Dan Rogers, Engineering a Device for Installing Dental Implants, Apr. 1992, Mechanical Engineering, pp. 72–73.
Brochure by *Krames Communications*, pp. 2, 3, 6–13, (1989).
Calcitek Advertisement, Integral Omniloc Fills the Gap, (1990), one page.
Brochure by *Nobelpharma*, pp. 1–6 (date unknown).
Advertisement by Implant Support Systems, Inc.: *Introducing a New Twist on Torque,* one page, (date unknown).
Brochure: Integral Omniloc, "*Prosthetic Tooling*", pp. 1, 2, PL–15, PL–21, (date unknown).
Brochure by Krames Communications, Understanding *Dental Implants: Comfort and Confidence Again,* pp. 1–15, 1288, (date unknown).
Brochure Academy of Osseointegration, *HA–Coated Tooth Replacement: The Integral Implant System,* 1991.

Primary Examiner—Edgar S. Burr
Assistant Examiner—Anthony H. Nguyen
Attorney, Agent, or Firm—Emrich & Dithmar

[57] ABSTRACT

A disposable, limited-use torque limiting wrench is provided having a predetermined maximum number of torque-applying cycles of use for applying a fixed torque to an adaptably connected driven member. This torque limiting wrench includes a rotatable casing including a slotted hub portion and a curved bias spring dimensioned to fit around the slotted hub portion. A dowel pin is also included having a center portion which is dimensioned to fit within and be gripped by a slot formed in the slotted hub portion and to be rotated thereby in response to a torque imparted on the rotatable casing. A torque ring is cooperatively engaged with the above by a predetermined number of pairs of radially extending and substantially equiangularly spaced slots. The respective ends of the dowel pin are uniquely dimensioned to fit within respective ones of the slots which become positioned colinearly therewith as the dowel pin is caused to be circumferentially rotated about the torque ring. The dowel pin ends move from an initial one of the pairs of slots to an adjacent pair of slots during each torque-applying cycle. The curved bias spring operates to bias the dowel pin into engagement with the torque ring. One of the pairs of slots is uniquely dimensioned such when the dowel pin engages therein after a final torque-applying cycle, the dowel pin is disengaged from the slotted hub portion under the urging of the bias spring.

20 Claims, 2 Drawing Sheets

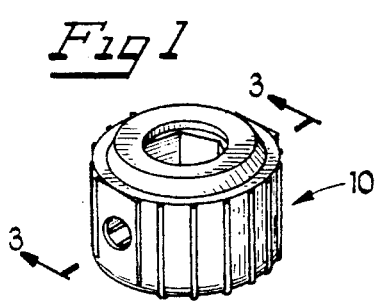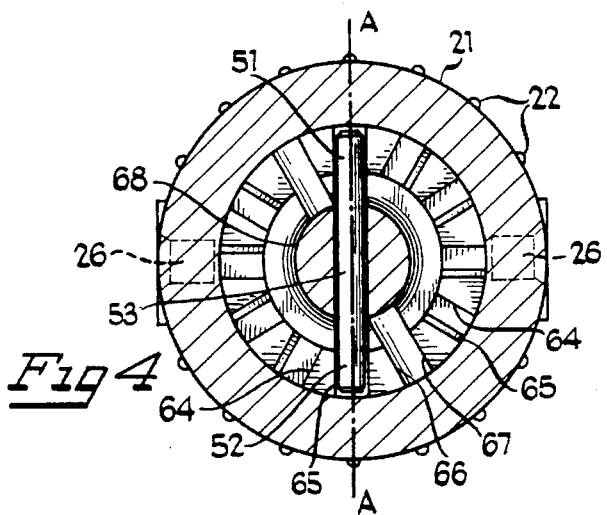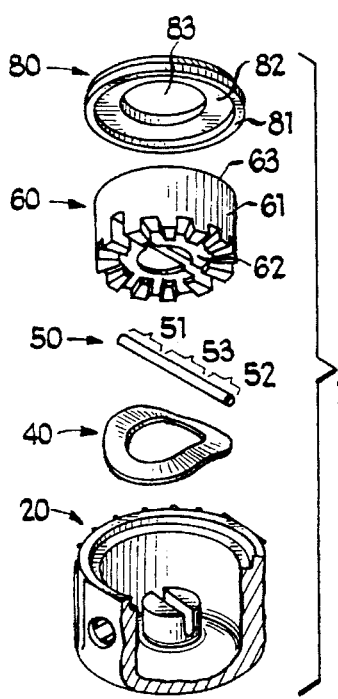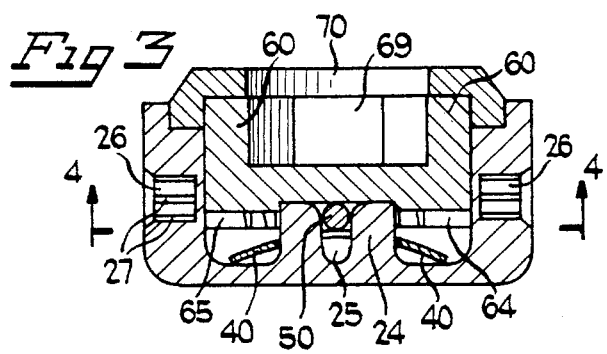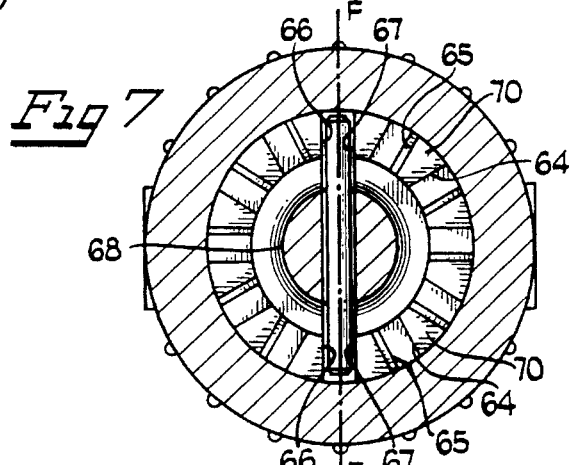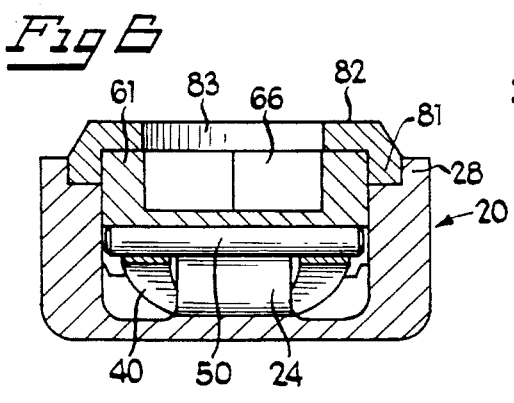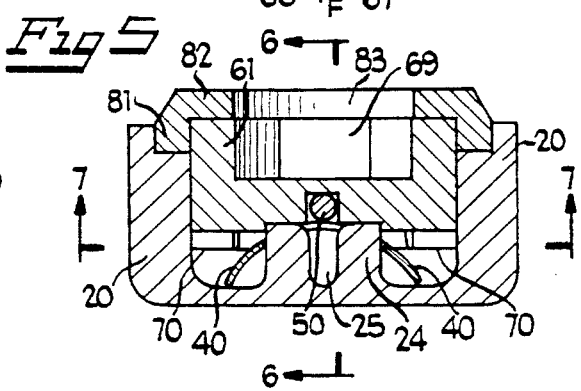

DISPOSABLE TORQUE LIMITING WRENCH

BACKGROUND OF THE INVENTION

1. Field of the Invention

The present invention relates generally to the field of restorative dentistry and, more particularly, to a prosthodontic torque limiting wrench provided with a torque limiting load spring for tightening dental implants.

2. Description of the Prior Art

Years of research has shown that living hard and soft tissues not only accept certain types of non-biological material, such as titanium, but also they actually incorporate it into the tissue itself. As a result, modern prostheses are being utilized in almost every facet of medical and dental science.

Prosthodontic restorative systems and techniques are well known in the prior art. For partially or fully edentulous patients, a dental implant fixture is implanted in a cylindrical bore made in a patient's jaw bone after the gum tissue has been displaced.

In the past few years, the use of dental implants has risen dramatically. Such implants typically consist of a titanium screw threaded into the patient's jaw bone and left alone for a number of months while the bone grows around it. On the top side, the screw (also called an anchor) contains a female threaded hole into which an adaptor (also known as an abutment) and a prosthetic attachment (such as a tooth or combination of teeth made, for example, of a composite material) are fastened. The fastening takes place after the implant has been sufficiently encapsulated in bone—a process that usually takes 3 to 6 months.

The torquing levels associated with the installation of the anchor, abutment and attachment units are usually different. Because each of these units is physically very small and made of highly malleable material, torque accuracy is critical. Over-torquing can easily damage the threads while under-torquing will cause the units to become unscrewed and loose in the mouth.

Torque-limiting devices, i.e., special-purpose prosthodontic wrenches for use with implants, used in the past are no longer sufficient given the increased emphasis on dental hygiene in recent years. Sterilization with torque-limiting prosthodontic wrenches is now routinely performed after use on any one patient to prevent infection of the next-to-use patient by communicable diseases, such as hepatitis or human immunodeficiency virus (HIV).

Precise and complete tightening of prosthodontic components in connection with dental restorations becomes difficult with torque-limiting wrenches whose precision has been degraded by the wear, tear and other such adverse effects of the sterilization process. For example, the most common and effective sterilization technique by dentists is the process of autoclaving. Repeated sterilization cycles of torque wrenches in an autoclave subjects such precision instruments to increased wear, including fretting and galling of metal parts. Some prior art instruments in particular are provided with complicated mechanical clutches that use lubricants. These instruments were found to be too heat sensitive to be adequately sterilized in an autoclave and as a result quickly became defunct in the current market.

The challenge to develop a torque-limiting mechanism that would provide long life and lasting calibration without the use of heat sensitive lubricants has lead to the development of an instrument by Implant Innovations, Inc. (I.I.I.) that operates to control torque with a strain-type system rather than by friction. This device is disclosed in an article by Dan Rogers entitled "Engineering a Device for Installing Dental Implants", Mechanical Engineering, April 1992, pp. 72–73. This I.I.I. torque driver is described as allowing the practitioner (dentist) to avoid the risks of over- or under-tightened screws and arguably offers the benefits of complete and adequate sterilization without degradation of precision. However, there remain disadvantages.

First, the strain-type system with the I.I.I. device referred to above includes two roller-coaster-type cams that face each other to transform a rotational force generated by turning the screw into the linear direction so that it can be applied to a strain gauge. The overall construction of this torque driver is, therefore, extremely complex, bulky, and expensive to manufacture, Secondly, because the I.I.I. torque driver device should be sterilized (e.g., in an autoclave) after its use on a patient, there remains the obvious risk that a practitioner may forget to sterilize the device before using it on the next patient.

SUMMARY OF THE INVENTION

It is a general object of the present invention to provide a high-precision torque limiting wrench which is economical and easy to manufacture.

It is another object of the present invention to provide a high-precision torque limiting wrench to be used by dentists and like practitioners, which torque limiting wrench has a limited life cycle to induce practitioners to dispose of the driver after its use on any one patient. Because the torque limiting wrench of the present invention is made disposable, the problems of degradation of torque accuracy and risk of patient cross-contamination common to prior art torque limiting wrenches, are almost entirely eliminated.

It is yet another object of the present invention to provide a torque limiting wrench the rotation of which imparts a predetermined high-accuracy torque to a driven member, such as an attachable bit, and thereby to a threaded fastener or the like, in a manner allowing the dentist to easily recognize when the proper torque has been applied; thus avoiding over- or under-tightening of dental attachments.

These and other features of the invention are attained by providing a non-reusable torque limiting wrench with a predetermined maximum number of usage cycles including a rotatable casing and a high-precision torque device for providing a fixed torque to a driven member adaptably connected thereto. The high-precision torque device provides a detectable fixed torque once during each usage cycle in response to the casing being rotated, and provides no torque thereafter. It is envisioned that this torque limiting wrench may be a prosthodontic-type torque wrench for use with dental implants.

Furthermore, the rotatable casing may be provided with a number of protruding ribs to facilitate rotation by hand and can include a receptacle for adaptably connecting a re-usable handle thereto.

The rotatable casing may also be color-coded to quickly guide the dentist in selecting a torque limiting wrench with a predetermined torque level. The torque limiting wrench components may also be ultrasonically welded together to prevent tampering and ease of disassembly.

More specifically, the high-precision torque limiting wrench includes a torque ring, a dowel pin coupled to the rotatable casing, and a curved bias spring urging the dowel pin into engagement with the torque ring with the fixed torque being proportionate to the bias load imparted by the curved bias spring.

The torque limiting wrench is intended to be made sufficiently small to permit hand tightening therewith by a practitioner by rotating said casing in a patient's mouth.

The torque limiting wrench may also be sufficiently labelled to remind the practitioner to discard it after use in the patient's mouth.

The preferred maximum number of usage cycles of the torque limiting wrench of the present invention is five.

The torque ring includes a plurality of radially arranged pairs of diametrically opposed protruding slots, each slot being defined by a vertical wall and a ramp. For each usage cycle, a moment arm is imparted to the dowel pin causing it to ride the respective ramps of an associated pair of protruding slots ultimately coming to rest (under the influence of a bias load from the bias spring) in the immediately radially-adjacent pair of protruding slots. The torque limiting wrench components cooperate in a fashion which allows the dentist to sense when a torque-applying usage cycle is completed.

It is yet a further object of the present invention to provide a non-reusable torque limiting wrench having a predetermined maximum number of usage cycles for applying a fixed torque to an adaptably connected driven member. This torque limiting wrench includes a rotatable casing including a slotted hub portion and a curved bias spring dimensioned to fit around the slotted hub portion. A dowel pin is also included having a center portion which is dimensioned to fit within and be gripped by a slot formed in the slotted hub portion and to be rotated thereby in response to a torque imparted to the rotatable casing. A torque ring is cooperatively engaged with the casing, the curved bias spring and the dowel pin and includes, on a first side thereof, a predetermined number of pairs of radially extending and substantially equiangularly spaced slots. First and second ends of the dowel pin are uniquely dimensioned to fit within respective ones of the slots which become positioned colinearly therewith as the dowel pin is caused to be angularly rotated about the torque ring. The dowel pin ends move from an initial one of the pairs of slots to an immediately adjacent pair of slots during each torque-applying usage cycle. The curved bias spring operates to bias the dowel pin into engagement with the torque ring. One of the pairs of slots is uniquely dimensioned such when the dowel pin engages therein, after the final usage cycle, the dowel pin is disengaged from the slotted hub portion under the urging of the bias spring.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood an appreciated.

FIG. 1 is a perspective view of a torque limiting wrench constructed in accordance with and embodying the features of the present invention.

FIG. 2 is an exploded, perspective view of the torque limiting wrench of FIG. 1 with a portion of the rotatable casing broken away to show internal structure.

FIG. 3 is an enlarged, vertical, sectional view taken generally along the line 3—3 in FIG. 1, showing the torque limiting wrench in an initial use position.

FIG. 4 is a horizontal sectional view taken generally along the line 4—4 in FIG. 3.

FIG. 5 is a view similar to FIG. 3 but illustrating the position of the torque limiting wrench after its final use.

FIG. 6 is a vertical sectional view taken generally along the line 6—6 in FIG. 5.

FIG. 7 is a horizontal sectional view taken generally along the line 7—7 in FIG. 5.

DETAILED DESCRIPTION OF THE PREFERRED EMBODIMENT

Figure 9:
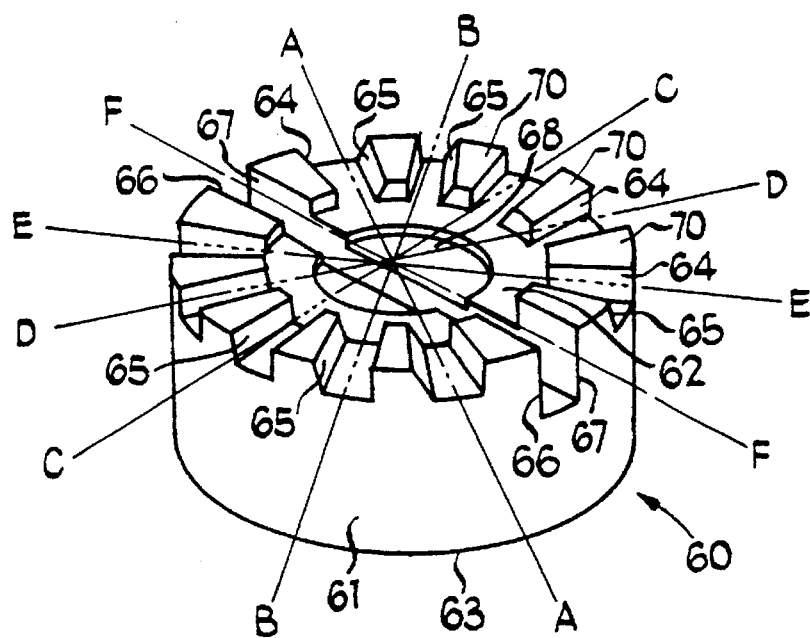
FIG. 9 is an enlarged, perspective, inverted view of the torque ring of the torque limiting wrench shown in the exploded view of FIG. 2.

Referring to FIGS. 1 and 2, there is illustrated a dental non-reusable torque limiting wrench, generally designated by the numeral 10, constructed in accordance with and embodying the features of the present invention. FIG. 1 shows a perspective view of torque limiting wrench 10 in its assembled, ready-to-use form.

The torque limiting wrench 10 is of a five-part construction as shown more clearly by the exploded view in FIG. 2 to be described below.

Torque limiting wrench 10 includes a casing 20, a curved bias spring 40, a dowel pin 50, a cam member in the nature of a torque ring 60, and, at an end opposite casing 20, a cover 80. The five elements recited above cooperate to define therebetween six pairs of radially extending and substantially equiangularly spaced slots with the slots of each pair diametrically aligned. Each pair of slots uniquely identifies one of five possible torquing operations for which the present embodiment is characteristically designed to provide.

Figure 8:
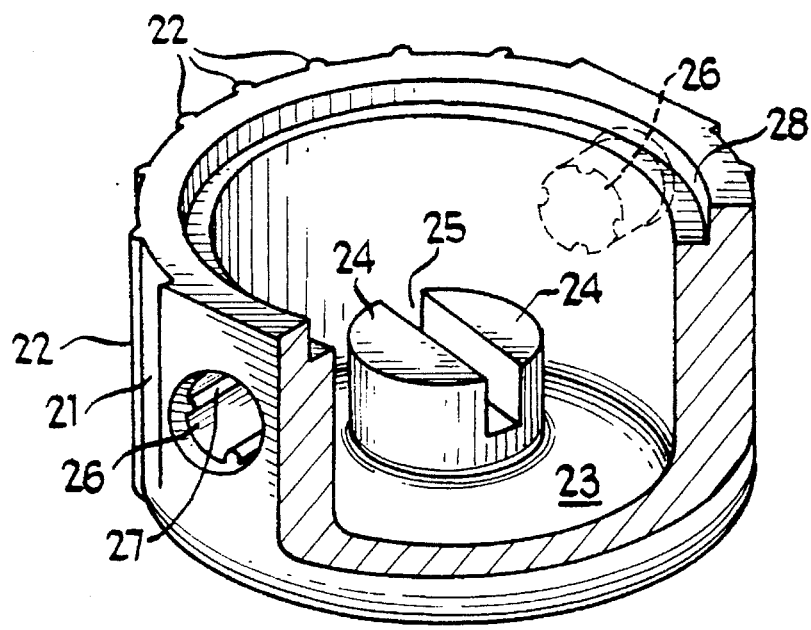
FIG. 8 is an enlarged perspective view of the rotatable casing of the torque limiting wrench shown in the exploded view of FIG. 2.

Referring also to FIG. 8, the casing 20 consists of a cylindrical wall 21 having, along an outer circumference thereof, a plurality of axially extending ribs 22 which facilitate finger-tightening of the torque limiting wrench 10 by a dentist. The cylindrical wall 21 is closed at one end by a base wall 23. Projecting from the base wall 23 coaxially within the cylindrical wall 21 is cylindrical boss 24 having a diametrical slot 25 formed in its distal end. Formed in the outer surface of the cylindrical wall 21 are diametrically opposed cylindrical cavities 26, each cylindrical cavity 26 extending a finite fixed distance along the width of cylindrical wall 21 up to a respective base wall therein. Spaced ribs 27 extend axially within each cavity 26 and project radially thereinto to facilitate gripping of an attachable handle (not shown) insertable therein. An attachable handle could be used to permit the dentist to rotate casing 20 in hard to reach places in the rear of a patient's mouth where finger-tightening would be difficult. Annular groove 28 is formed in the open end of the cylindrical wall 21.

The curved bias spring 40 is preferably an annular metallic-type flexible washer spring with a curved profile of known maximum load resistance.

The dowel pin 50 is preferably a metallic, cylindrical pin having end portions 51, 52 and mid-portion 53.

A description of torque ring 60 herein follows with reference also to FIG. 9. Torque ring 60 essentially consists of a cylindrical body 61 with a first base surface 62 at one end and a second base surface 63 at an opposite, distal end. First base surface 62 having, circumferentially arranged, six pairs of radially extending and substantially equiangularly spaced slots, with the slots of each pair diametrically aligned and designated by associated axes lines A—A to F—F respectively. All slots associated with axes lines A—A to E—E are of equal size and dimensions, each such slot being defined by a vertical wall 64 and a ramp 65 and forming a cam portion. By contrast, the slots formed by vertical walls 66 and 67 associated with axis line F—F form release portions which are significantly deeper and include no inclined (ramp) portion for reasons to be explained below. Torque ring 60 further includes a circular recessed portion 68 which is dimensioned to engage with the annular end surface of cylindrical boss 24 of casing 20. Additionally, second base surface 63 includes a hex receptacle 69 for matingly engaging with a hexagonal body driver bit (not shown), such as for example a screwdriver-type attachment. Radially extending slots defined by axes lines A—A to F—F are substantially separated from adjacently disposed slots by flat adjoining surfaces 70. Dowel pin 50 is dimensioned to fit transversely within each of the six pairs of slots which are formed on first base surface 62 and also has a length substantially equal to the diameter of torque ring 60.

The cover 80 is used to lock (snap) into position torque ring 60, dowel pin 50 and curved bias spring 40 within casing 20 following assembly thereof in the manner to be described below. Cover 80 is an annularly shaped cap which includes at a first end, along an outer periphery thereof, a lip 81 which is dimensioned to engage with the annular groove 28 in the open end of the cylindrical wall 21. A base end wall 82 extends inwardly from a top end of the cover 80. An exposed cavity portion 83 in base end wall 82 is provided and dimensioned to permit hex receptacle 69 of torque ring 60 to receive, prior to torquing, an appropriate type driver bit as described above.

Casing 20, torque ring 60 and cover 80 may be constructed from plastic or like material and injection molded into the shape generally shown in the drawings.

During initial assembly of torque limiting wrench 10, casing 20, curved bias spring 40, dowel pin 50, torque ring 60 and cover 80 are all snapped into the initial position shown more accurately by the cross-sectional views of FIGS. 3 and 4. The curved bias spring 40 is initially placed around cylindrical boss 24 resting on base wall 23. The spring tension (load) of curved bias spring 40 is of known value and uniquely selected to impart a correlative torque level per torque-applying usage cycle (i.e., a fixed spring load during each torquing operation). Dowel pin 50 is placed over curved bias spring 40 extending transversely within diametrical slot 25 such that dowel pin ends 51 and 52 make contact with respective portions of curved bias spring 40 as shown in FIG. 3 for cooperation therewith to form a resilient cam following structure. Curved bias spring 40 imparts a bias load on the dowel pin 50 to keep it suspended above the base of diametrical slot 25.

Once curved bias spring 40 and dowel pin 50 have been positioned in casing 20 in the manner described above, torque ring 60 is then slidably inserted within cylindrical wall 21 so that the dowel pin ends 51 and 52 are arranged to engage with the respective opposing slot pair ends of torque ring 60 defined by axis line A—A, as shown more clearly in FIG. 4. This will depress the pin 50 into the diametrical slot 25 against the urging of bias spring 40, with the boss 24 being received in the recessed portion 68 of the torque ring 60.

In this position, dowel pin ends 51 and 52 are abuttingly held against the slotted grooves of torque ring 60 in response to an axially imparted spring load by curved bias spring 40 which functions to prevent dowel pin 50 from becoming disengaged from its present position against a respective one of the opposing slot pair positions.

Prior to torquing, cover 80 is used to lock into position torque ring 60, dowel pin 50 and curved bias spring 40 within casing 20. This is achieved by engagingly coupling annular groove 28 of casing 20 with lip 81 of cover 80 providing a secure, tight fit therewith. Thus, casing 20, curved bias spring 40, dowel pin 50, torque ring 60 and cover 80 are cooperatively constructed to easily snap together during assembly. The finished product is intended to be ultrasonically welded to prevent tampering and disassembly thereof.

An attachable driver bit (not shown) of appropriate dimensions is then finally inserted into hex receptacle 69 (and extending through exposed cavity portion 83 of cover 80) in preparation for torquing.

The operation of the torque limiting wrench 10 of the present invention, will now be described in connection with FIGS. 3–7. Referring to FIGS. 3 and 4, prior to initial torque limiting wrench use, dowel pin 50 will reside in the initial position about torque ring 60 defined by axis line A—A. As previously explained, each of the slots or cam portions defined by axes lines A—A to E—E—provided along the surface of the torque ring 60 facing dowel pin 50, curved bias spring 40 and base wall 23 (of casing 20)—is respectively defined by a vertical wall 64 and a ramp 65. During a torque-applying cycle, the dentist, in an effort to tighten a dental implant element such as an anchor, abutment or some related prosthetic attachment thereto, will exert a rotational force on casing 20. This rotational force will be transmitted by way of cylindrical boss 24 onto dowel pin 50 causing it to angularly rotate about mid-portion 53 which is dimensioned to fit within cylindrical boss 24 and upwardly biased against torque ring 60 by curved bias spring 40.

Thus, when casing 20 is rotated, since a mid-portion 53 of dowel pin 50 extends through cylindrical boss 24 of casing 20 causing dowel pin 50 to rotate therewith, dowel pin ends 51 and 52 (initially situated in opposing slots about axis line A—A) are urged to engage with and ride up the respective abutting inclined ramp 65. This riding action of the dowel pin 50 on torque ring 60 will impart a rotational torque on torque ring 60 causing it to rotate; the direction of rotation being the same angular clockwise direction as the initial direction of rotation of casing 20. Assuming a driver bit (not shown) is attached at a first end thereof to hex receptacle 69 of torque ring 60 and at an opposite end thereof to the specific dental element to be tightened, then during a torque-applying cycle, a torque level equal in value to that imparted on torque ring 60 will also be imparted on the driver bit and in turn cause it to apply a torque of equal value on the element being tightened therewith. Once the dowel pin ends 51 and 52 have successfully traversed respective abutting ramps 65 as well as the flat adjoining surfaces 70 leading to the vertical wall 64 of the subsequent opposing pair of slots, the torque-applying cycle would have been completed and the dentist would have detected (sensed) this occurrence by the increasing torque resistance at the beginning of the torque-applying cycle which is then followed by a decreasing torque resistance at the end of the same torque-applying cycle.

During an initial first torquing operation, dowel pin 50 is caused by the cooperation of casing 20 and curved bias spring 40 to become rotatingly displaced from its initial position in the opposing slot pair positions characterized by axis line A—A in FIGS. 4 and 9, to the clockwise adjacently situated position defined by axis line B—B. Similarly, during the next and all subsequent torquing operations, dowel pin 50 will again be caused to become rotatably repositioned in an adjacent slot pair position. Consequently, following completion of an initial torque-applying cycle of use (i.e., the first torquing operation), dowel pin 50 will have been caused to rotate from the initial position defined by axis line A—A to a new position defined by axis line B—B. In a similar manner, during a second torque-applying usage cycle, dowel pin 50 will rotate from a position defined by axis line B—B to a position defined by axis line C—C. By the same token, during a third usage cycle, the dowel pin position will rotate from its current position about axis line C—C position to a new position about axis line D—D. Following a fourth torque-applying cycle of use, the dowel pin position will rotate from its position about axis line D—D to a position about axis line E—E. Finally, during the fifth and final usage cycle, dowel pin 50 will rotate from its previous position about axis line E—E, to its final position relative to torque ring 60 defined by axis line F—F. Once dowel pin 50 has been rotated about torque ring 60 becoming secured in the diametrically opposed release portion pair of slots defined by axis line F—F, casing 20 (more particularly, cylindrical boss 24) will be caused to release its grip on dowel pin 50. In this position, further tightening by torque limiting wrench 10 becomes impossible as will be explained more fully below.

In more general terms, each torque-applying cycle can be characterized by the angular displacement of dowel pin 50 from one of diametrically opposed pair of slots A—A to E—E to a circumferentially adjacent pair of slots B—B to F—F, respectively. Throughout a torque-applying cycle, a dentist will be able to feel (sense) the displacement effect of dowel pin 50 about torque ring 60 and will thus be immediately alerted of the end of each torquing operation. More specifically, the dentist will know when dowel pin ends 51, 52 have fallen into the slots of the adjacently disposed pair of slots indicating to him that no more torque should be applied to the casing 20.

The final position of dowel pin 50 following the fifth and final torquing operation will now be described in connection with FIGS. 5–7 and 9. As shown in FIG. 9, the opposing slot pair defined by axis line F—F consists of one long groove (formed by deep vertical walls 66, 67) which is significantly deeper than the previous five axes lines A—A to E—E position grooves and which characteristic feature is also that it includes no ramp at either end. As a result, when dowel pin 50 is rotated into position within axis line groove F—F, curved bias spring 40 will urge dowel pin 50 to become seated entirely within axis line groove F—F, becoming entirely disengaged from slot 25 of cylindrical boss 24 of casing 20 as shown in FIG. 5.

In this final position, should the dentist attempt to rotate casing 20 by either finger-tightening or, alternatively, by attaching a non-disposable handle thereto, casing 20 will merely free-spin (free-wheel) relative to dowel pin 50 which has become immovably lodged within axis line groove F—F of torque ring 60 by the spring loading tension of curved bias spring 40. Consequently, dowel pin 50 can impart no angular force on the torque ring 60 and, by implication, the torque ring 60 can impart no force on an attached driver bit (not shown). The torque limiting wrench 10 will thus become non-usable and the dentist will be forced to discard it thus substantially precluding the risk of cross-contamination of a communicable disease from a first-to-use patient to a next-to-use patient.

An essential attribute of the present invention is that there are only a limited (namely five) number of torquing operations for which torque limiting wrench 10 is useful. Thereafter torque limiting wrench 10 becomes non-reusable and must necessarily be discarded by the user. If the user is a dentist or similar such practitioner, the non-reusable feature of the present device, in cooperation with the fact that the device is good for only five torquing operations, will successfully induce the dentist to dispose of the torque limiting wrench 10 after its use on any one patient. Any and all attachable driver bits and handles (not shown), such as screwdriver attachments and the like, used with torque limiting wrench 10 during the limited number of torque-applying usage cycles, can be (once detached therefrom) properly sterilized—using conventional sterilization processes—and used again.

Different dental implant elements and attachments necessarily require different torquing levels. For example, when installing an anchor jaw in the patient's jawbone, a typical manufacturer recommended torque level is roughly 10 Newton-cm (10 N•cm). By comparison, when tightening (screwing) a temporary healing cuff into the anchor jaw, a recommended torque level is in the order of 20 N•cm. Similarly, the recommended torque level when installing a final abutment is approximately 30 N•cm. Because each torque limiting wrench 10 of the present invention is factory calibrated to apply a predetermined torque level only, a dentist must select a 10 N•cm torque limiting wrench to install the anchor jaw, a 20 N•cm torque limiting wrench to install the temporary healing cuff into the anchor jaw, and a 30 N•cm torque limiting wrench to tighten the final abutment. When practicably possible, the same or different driver bits (screwdriver attachments) may be used interchangeably. Once all the dental elements have been accurately torqued and properly installed, all three torque limiting wrenches should be discarded. Driver bits are reusable and should be saved and sterilized (to avoid cross-contamination) for reuse with new torque limiting wrenches 10. Because simple attachments such as driver bits and handles provide no calibration specific function, such attachments are generally made very durable to protect them against structural damage in an autoclave.

The bias load imparted by the curved bias spring 40 is a function of the load resistance properties of the spring itself. Consequently, different tension springs will invariably affect the torque level accuracy of torque limiting wrench 10. On these facts, although torque limiting wrench 10 generates a given torque level by the cooperation of casing 20, curved bias spring 40, and dowel pin 50 about the uniquely dimensioned slots defined by axes lines A—A to F—F of torque ring 60, it is possible to make a number of different torque limiting wrenches 10 each providing a different torque level using identical (size and shape) components—only the bias load of the respective curved bias spring 40 being different. For example, a 10 N•cm torque limiting wrench will comprise an identical shape and size casing 20, dowel pin 50, torque ring 60 and cover 80 as would a 20 N•cm torque limiting wrench. The difference between them will reside in the load bias (tension) of the curved bias spring 40 to be specifically incorporated in each of the two different torque level drivers. By comparison, the curved bias spring 40 in the 20 N•cm torque limiting wrench will impart a load bias almost twice that of a similarly shaped curved bias spring 40 to be incorporated in the 10 N•cm torque limiting wrench.

Given the fact that the spring load provided by the curved bias spring 40 is directly related to the torque accuracy level, a variety of different high precision torque wrenches of varying torque capacities can be assembled merely by varying the load bias of the curved bias spring 40 to be incorporated therein. This is a tremendous advantage over prior art torque wrenches which required very complex calibrating units, such units being susceptible to damage when sterilized.

Also because a great variety of torque limiting wrenches 10 can be provided during assembly thereof by merely appropriate bias load selection of the curved bias spring 40 to be incorporated therein, the non-reusable torque limiting wrenches 10 of the present invention can be made easily and economically and pre-assembled with a high degree of precision (5% tolerance) to provide the necessary torque levels for the appropriate phase of a dental implant procedure.

Additionally, because each torque limiting wrench 10 used by a dentist is torque level specific, a dentist must not only be aware of the recommended torquing level for the dental implant element to be tightened, but must also have knowledge of the torque-applying capacity of each and every torque limiting wrench 10 available to him. To facilitate a dentist's selection of the proper load torque limiting wrench 10, each torque limiting wrench 10 once assembled may be uniquely color coded (or, alternatively, conspicuously stamped) to more quickly guide the dentist to the disposable torque limiting wrench providing the torque precision level for the procedure involved.

Because the torque limiting wrench 10 of the present invention is designed to have a limited number of torque-applying use cycles, dentists will quickly become conditioned to dispose of it after each patient-use—even if used only once.

The simple construction of this device will also inevitably result in economical scales of production, with the ultimate effect of low retail cost per unit; as a result of which, there would be little or no cost benefit to a dentist reusing a potentially contaminated torque limiting wrench on a different patient and would thus be motivated to dispose of it as intended.

Furthermore, given the very limited number of possible torquing operations for which the torque limiting wrench 10 of the present invention may be said to have a useful life, it is believed that dentists will inherently be deterred from attempting to sterilize used torque limiting wrenches 10 rather than properly dispose of them. This is because the time and cost benefits of doing so weigh heavily in favor of discarding a potentially contaminated torque limiting wrench 10 after use on any one patient rather than attempting to sterilize and reuse it.

While the non-reusable torque limiting wrench 10 of the present invention is ultimately non-reusable, designed with the purpose of disposing it after use on any one patient, the driver bit and handle attachments (not shown) are uniquely detachable and therefore reusable upon their adequately being sterilized in an autoclave.

Furthermore, because only the non-reusable torque limiting wrenches 10 are discarded after use on any one patient but not the reusable driver bits or handles used therewith, these special purpose torque limiting wrenches 10 of the present invention are a significant improvement over prior art devices.

From the foregoing, it can be seen that there has been provided an improved high-precision prosthodontic torque wrench, which is disposable, economical and easy to manufacture, which has a useful life cycle of five uses, and which is adaptable for a variety of applications.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. A torque limiting wrench for applying up to a predetermined maximum torque to an associated driven member during each of a plurality of torque-applying cycles, said wrench comprising: a rotatable casing; a cam member adapted for coupling to the driven member and having a plurality of sequentially arranged portions including a predetermined number of cam portions and a release portion; and resilient cam following structure coupled to said casing for resilient engagement with said cam portions and with said release portion, said cam following structure, when in engagement with a cam portion, being responsive to rotation of said casing during a torque-applying cycle for rotating said cam member until the predetermined torque is reached, whereupon said cam following structure shifts to engagement with the next successive portion, said cam following structure, when in engagement with said release portion, being unresponsive to rotation of said casing and thereby preventing further engagement of said cam following structure with a cam portion of said cam member.

2. The torque limiting wrench of claim 1, wherein said torque limiting wrench is a prosthodontic-type torque wrench for use with dental implants.

3. The torque limiting wrench of claim 1, wherein said rotatable casing includes a number of protruding ribs to facilitate rotation by hand.

4. The torque limiting wrench of claim 2, wherein said rotatable casing includes means for connecting a re-usable handle thereto.

5. The torque limiting wrench of claim 3, wherein said wrench is made small to permit hand tightening therewith by a practitioner by rotating said casing in a patient's mouth.

6. The torque limiting wrench of claim 5, wherein said torque wrench is labelled to remind the practitioner to discard it after use in the patient's mouth.

7. The torque limiting wrench of claim 1, wherein said resilient cam-following structure includes a curved bias spring for imparting a predetermined bias force, and a dowel pin coupled to said rotatable casing, the value of the predetermined maximum torque being proportionate to a maximum value of the predetermined bias force imparted by said curved bias spring during each torque-applying cycle.

8. The torque limiting wrench of claim 7, wherein said torque ring includes a plurality of pairs of radially extending and diametrically opposed slots with the pairs being equiangularly spaced, each slot being defined by a vertical wall and a ramp, respective ends of said dowel pin being moved against associated ramps of a pair of slots in response to said casing being rotated to become repositioned in an adjacent one of said pairs of slots.

9. The torque limiting wrench of claim 8, wherein said casing is manually rotatable by a wrench operator, the repositioning of said pin at the end of each torque-applying cycle producing a tactile indication that the torque-applying cycle has been completed.

10. The torque limiting wrench of claim 1, wherein said predetermined number is five.

11. The torque limiting wrench of claim 1, wherein said rotatable casing is color-coded to reflect a value associated with the value of the predetermined maximum torque.

12. The torque limiting wrench of claim 1, wherein said torque wrench is ultrasonically welded to prevent tampering.

13. A torque limiting wrench for applying up to a predetermined maximum torque to an associated driven member during each of a plurality of torque-applying cycles, said wrench comprising:

a rotatable casing including a hub portion having a transverse slot;

a pin, received in the slot to be rotated by said hub portion in response to rotation of said casing; and a torque ring having a plurality of radially extending and sequentially arranged slots facing said pin, said slots including a predetermined number of first slots each having a ramp surface and a second slot following said first slots, said pin being receivable in each of said slots, and a bias spring resiliently urging said pin against said torque ring and resisting displacement of said pin from a slot in which it is received, said pin when received in each one of said first slots rotating said torque ring in response to rotation of said casing until the predetermined maximum torque is reached whereupon said pin cams out of said each one of said first slots and shifts to the next successive slot terminating a torque-applying cycle, said second slot being shaped and dimensioned such when the pin engages therein after a final torque-applying cycle, the pin becomes disengaged from the slot of said casing under the urging of said bias spring.

14. The torque limiting wrench of claim 13, wherein said radially extending sequentially arranged slots are arranged in diametrically aligned pairs.

15. The torque limiting wrench of claim 13, wherein said bias spring is a curved annular washer engaged within said casing around said hub portion.

16. The torque limiting wrench of claim 13, wherein each slot is provided with only one ramp surface, said pin being engaged to cam out of each first slot by riding its respective ramp surface.

17. The torque limiting wrench of claim 13, wherein said second slot is deeper than said first slots.

18. The torque limiting wrench of claim 13, wherein said first slots and said second slot are substantially equiangularly spaced.

19. The torque limiting wrench of claim 13, wherein said predetermined number of first slots is ten.

20. The torque limiting wrench of claim 15, wherein the value of the predetermined maximum torque is proportionate to a spring load resistance of said bias spring.

* * * * *